US007059180B2

(12) United States Patent
Al-Ghamdi

(10) Patent No.: US 7,059,180 B2
(45) Date of Patent: Jun. 13, 2006

(54) WATER CUT RATE OF CHANGE ANALYTIC METHOD

(75) Inventor: Abdulla H. Al-Ghamdi, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 0 days.

(21) Appl. No.: 10/167,294

(22) Filed: Jun. 10, 2002

(65) Prior Publication Data

US 2003/0226396 A1    Dec. 11, 2003

(51) Int. Cl.
*G01N 33/26* (2006.01)
*G06F 17/17* (2006.01)

(52) U.S. Cl. .............................. 73/152.42; 73/152.02; 73/152.18; 73/152.39; 73/152.46; 702/6; 702/12; 702/16

(58) Field of Classification Search ............... 73/61.43, 73/61.44, 861.04, 152.02, 152.05, 152.06, 73/152.08, 152.18, 152.23, 152.39, 152.41, 73/152.44, 152.55, 152.42; 166/248, 372; 702/6, 12, 16
See application file for complete search history.

(56) References Cited

U.S. PATENT DOCUMENTS

| 3,402,768 | A | * | 9/1968 | Felsenthal et al. | 166/245 |
|---|---|---|---|---|---|
| 3,525,258 | A | | 8/1970 | Fowler et al. | 73/155 |
| 3,795,278 | A | * | 3/1974 | Whitten et al. | 166/272.5 |
| 4,364,431 | A | * | 12/1982 | Saidi et al. | 166/275 |
| 4,660,414 | A | * | 4/1987 | Hatton et al. | 73/61.44 |
| 4,673,040 | A | * | 6/1987 | Sydansk | 166/305.1 |
| 5,586,027 | A | | 12/1996 | Carlson et al. | 364/422 |
| 5,597,961 | A | * | 1/1997 | Marrelli | 73/861.04 |
| 5,752,570 | A | * | 5/1998 | Shaposhnikov et al. | 166/372 |
| 5,764,515 | A | | 6/1998 | Guerillot et al. | 364/420 |
| 5,857,519 | A | * | 1/1999 | Bowlin et al. | 166/105.6 |
| 6,000,468 | A | * | 12/1999 | Pringle | 166/53 |
| 6,052,520 | A | | 4/2000 | Watts, III | 395/500.31 |
| 6,101,447 | A | | 8/2000 | Poe, Jr. | 702/13 |
| 6,321,840 | B1 | * | 11/2001 | Billiter et al. | 166/268 |
| 6,372,123 | B1 | * | 4/2002 | Kresnyak et al. | 208/187 |
| 2002/0139197 | A1 | * | 10/2002 | Salamitou et al. | 73/861.04 |
| 2003/0170077 | A1 | * | 9/2003 | Herd et al. | 405/224.2 |

FOREIGN PATENT DOCUMENTS

RU    2060366 C1 *    5/1996

OTHER PUBLICATIONS

Beyer, William H., "CRC Standard Mathematical Tables and Formulae", CRC Press, 1991, pp. 174-175.*

(Continued)

*Primary Examiner*—Hezron Williams
*Assistant Examiner*—David A. Rogers
(74) *Attorney, Agent, or Firm*—Abelman, Frayne & Schwab

(57) ABSTRACT

A method of measuring a water effect on an underground non-water well includes the steps of assembling a history of water cut (WC) measurements for the well over an extended period of time, determining a water cut rate of change (R) for the well based upon the history of water cut measurements, wherein the water cut rate of change is defined as follows:

$$\frac{d(WC)}{d(t)} = R,$$

and identifying whether an anomaly exists based on the determined R.

17 Claims, 10 Drawing Sheets

OTHER PUBLICATIONS

Epic Consulting Services, "ResAssist for Windows—Understanding Your Watershed", Apr. 2002, p. 2.*

Robertson et al., "A System Engineering Approach to Field Development", Society of Petroleum Engineers, Sep. 2001, p. 4.*

"Network News", Jun. 2000, Petroleum Technology Transfer Council, vol. 6, No. 2, p. 2.*

"Recovery of Bypassed Oil in the Dundee Formation Using Horizontal Drains", Michigan Technological University, 1994, Available online at <http://www.geo.mtu.edu/svl/michproj/intro.html>, see link to <http://www.geo.mtu.edu/svl/michproj/maps/crys_hor.htm>.*

Vance,Harold, "Preferred WAterflood Management Practices for the Scraberry Trend Area", Sep. 26, 2002.*

* cited by examiner

WATER CUT RATE OF CHANGE ANALYTIC METHOD

FIELD OF THE INVENTION

This invention relates to the measurement of water in oil wells.

BACKGROUND OF THE INVENTION

Oil wells are usually dry when first drilled, which means that they produce only oil. However, after an oil well has been in production for a period of time, which may be ten to fifteen years or more, the well may begin to co-produce water with the crude oil flow. The water is typically an incursion from a local aquifer that begins to move through the reservoir rock as the oil pressure is lowered. The more water wet the well becomes, the lower the net oil rate is, to the point where the water production becomes too high to be lifted to the surface. At this point, the percentage of oil in proportion to the water cut may be so low, or be reduced to zero, so as to take the well out of production. Therefore, water production must be controlled so as not to lose oil production.

In addition to naturally occurring water incursions, it is often the practice to pump or allow water to flow under the influence of gravity into bore holes in the vicinity of the oil production area, in what is called water injection, to maintain reservoir pressure and sweep oil towards production wells. In this context, the sweep efficiency is defined as the percentage of oil being swept by water. The definition of 100% sweep efficiency is that oil is completely swept by water in a piston-like displacement, which is never the case in physical applications. Usually injected water will finger through the oil and bypass some oil. Poor sweep efficiency is a result of water bypassing most of the oil by channeling through and reaching the oil producing wells. This in return will result in loss by leaving oil in the ground.

The severity of water production is conventionally measured by water cut percent, measuring produced fluid rates by meters at the surface and calculating the water cut from the measured water and oil rates at surface conditions. Water cut is defined as the percentage that the water rate represents of the total rate of a well or:

$$WC = \frac{q_w}{q_w + q_o} \times 100\% \quad (1)$$

Where:
 WC=water cut
 $q_o$=oil rate
 $q_w$=water rate

Hence, a well producing at 50% water cut is more severely affected than a well producing at 30% water cut.

Depending upon the nature of the geological formation, and particularly on faults or discontinuities in the reservoir rock structure, the water may flow unevenly in lateral and vertical directions from the point of its injection. Thus, water fed into the oil reservoir formation at one point may quickly advance to a producing well and appear as a water cut whose value, or percentage of total flow, increases over time. Other portions of the injected water may serve their intended purpose which is to provide a pressure to force the oil in the reservoir rock to move towards the producing well.

In accordance with long-standing practices in the oil exploration and production industry, the historical value of the water cut is maintained for each well in any given field throughout the life of the well, which runs in the tens of years in some cases.

In the past, the absolute value of the water cut at any given time has been considered the most relevant information from the standpoint of managing the overall production from wells in the field. This has been the practice, even though historical data may be available for time periods of ten, twenty or even forty years in highly productive fields.

SUMMARY OF THE INVENTION

It is therefore an object of the present invention to provide a method that avoids the above-described difficulties of the prior art.

In accordance with the present invention, a new analytical tool is based upon a newly defined "water cut rate of change" over extended periods of time, and for the current period, e.g., one year. The data is used to identify anomalies, e.g., where the water cut rate of change (WCRC) is greater than 10%. Wells exhibiting such anomalies are termed anomalous wells.

More specifically, a method of measuring a water effect on an underground non-water well comprises the steps of assembling a history of water cut (WC) measurements for the well over an extended period of time, determining a water cut rate of change (R) for the well based upon the history of water cut measurements, wherein the water cut rate of change is defined as follows:

$$\frac{d(WC)}{d(t)} = R,$$

and identifying an anomaly based on the determined R.

These anomalous wells can be graphically portrayed by converting the data for reproduction on so-called "bubble maps". A bubble map is an aerial map in which the value of the WCRC is portrayed graphically in a circle having a diameter proportional to the WCRC value as measured in a percentage. Using this technique, it is easy to determine where the flow of water has been increasing at a greater rate as compared to other wells in the area or region.

A similar graphical plotting technique can utilize bars or rectilinear symbols that are proportional in size to the relative value of the WCRC for each well.

The improvement provided by the WCRC method is that it takes into account the relative rate of change as opposed to the absolute value of the water cut when last measured for any given well or group of wells in the area of interest. For example, a water cut that has increased from ten to fifty percent in a twelve-month period represents a more significant event than a water cut that has increased from fifty percent to sixty percent, even though the value at the latter well is greater in absolute terms.

Accordingly, the inventive WCRC method is useful in:
1. oil reservoir management
2. reservoir characterization
3. reservoir simulation, and
4. production strategies.

This method also permits the rapid identification of geological and oil field heterogeneities and anomalies.

These and other objects, features and advantages of the present invention will be apparent from the following detailed description of the preferred embodiments taken in conjunction with the following drawings, wherein like reference numerals denote like elements.

DETAILED DESCRIPTION OF THE PREFERRED EMBODIMENTS

Figure 1:
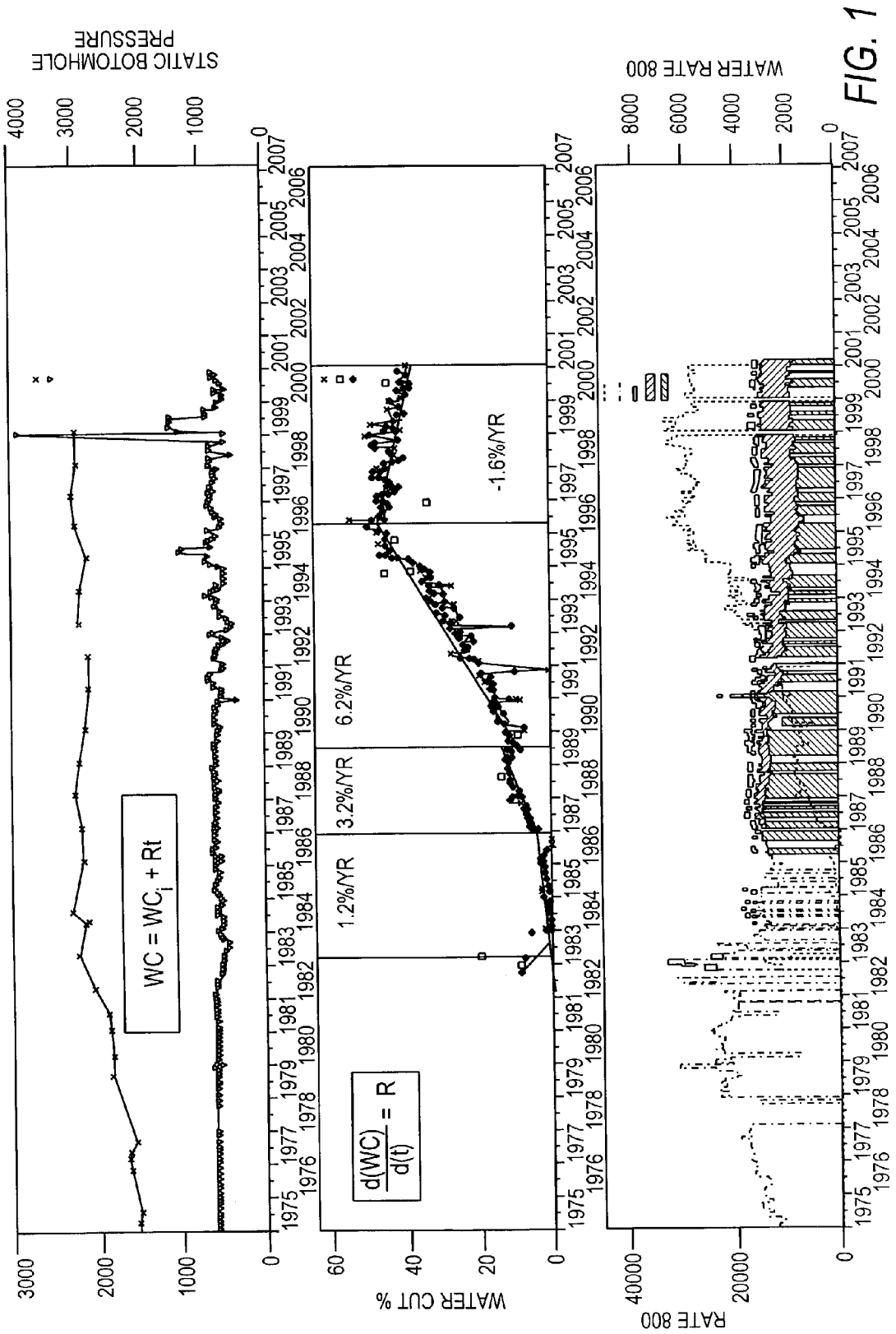
FIG. 1 is a well history plot illustrating the method in accordance with a preferred embodiment of the present invention.

As described above, the prior art has been concerned with water cut percentage at a certain point of time as defined above in units of percent. However, the new WCRC technique has to do with the rate of change of water cut over time and its unit is in percent per unit time, e.g. percent per year or percent per month.

In addition, while the prior art dealt with the current measured water cut percentage, WCRC encompasses historical water cut behavior including the present and then is used to predict future performance. WCRC is obtained through manipulating the measured water cut by calculating the derivative or rate of change of water cut percentage with respect to time.

Definition of the Linear WC Rate of Change (WCRC)

The definition of WCRC is as follows. Assume a linear WC that increases with respect to time. Therefore, WC at any point of time is equal to the initial $WC=WC_1$ plus the WCRC or "R" multiplied by time.

$$WC = WC_1 + Rt \qquad (2)$$

By differentiating this equation, we obtain the constant R representing the WCRC.

$$\frac{d(WC)}{d(t)} = R \qquad (3)$$

As can be clearly seen from Equation 3, one important property of the WCRC method is its independence of water cut, which is demonstrated by the following example. Assume there are two wells, where well A is currently producing a water cut of 10% while well B is producing at a water cut of 60%. In one-year period, assume the water cut in well A increases to 50% while the water cut in well B increases to 70%. Therefore the WCRC for well A is 50% minus 10% which is equal to 40% per year, while the WCRC for well B is 70% minus 60% or 10% per year.

Accordingly, although well B was cutting water by six times as much as well A to start with and almost 50% more after one year, well A is still more anomalous than well B. Indeed, based on their calculated WCRC values, well A is four times as anomalous as well B.

There is a further impact on water production. Assume that well B is located three times the distance to a water-producing fault as well A. Due to their relative proximity to the fault, the following would be expected:

1) Well A will start producing water earlier than well B.

2) Well A will also have a faster increase in water cut than well B.

In order to correlate the first property of earlier water production, all the wells must have been drilled at the same time, which is generally not the case in the real world. Therefore, the second characteristic of the water cut rate change will be used as the basis for the identification of anomalous areas with high or hyper water production.

For the purpose of the following examples, WCRC cutoff valves of 10% and 15% were used in order to classify producing wells as normal or anomalous. However, this cutoff is application-dependent and more accurate application-specific cutoff values can be calculated for different applications on case-by-case basis.

Segmented WCRC Methodology

The methodology for the calculation of the WCRC technique can be summarized as follows:

1. WCRC is calculated from historical water cut behavior of each well for all the wells in the study area.

2. A WCRC cutoff value of 10% or 15% is used in order to identify wells of hyper water production.

3. A minimum of 1 year historical trend is used to calculate representative WCRC values.

4. WCRC values are next plotted as a bubble or a bar on a field map, where the size of each bubble or bar corresponds to the WCRC value.

5. The bubble (bar) map representation serves as a powerful and insightful tool to identify anomalous areas of high and hyper water production, which can be correlated with the well distance to the fault.

Continuous WCRC Methodology

The WCRC technique described above can be automated and more accurately calculated using a computer program that will calculate the continuous derivative by one of the well known and available mathematical algorithms. The program could then plot the resulting WCRC values on the same map. Automation of WCRC calculation and plotting will dramatically improve the speed and accuracy of the technique.

Once the bubble map is generated, by either methodology, it can be utilized to identify areas of high and hyper water production. From the formation of clusters of bubbles, one can deduce whether a cluster is pointing to the existence of reservoir heterogeneities and whether water is coming vertically or laterally. In the case of a water flood project, one can see if the injected water is sweeping oil efficiently or if it is advancing in an uneven fashion, and therefore one can apply well control in order to achieve optimum sweep efficiency.

FIG. 1 shows the well history plot for a sample well, called SDGM-4, which will be employed to illustrate the segmented approach of the new WCRC analysis technique.

In order to calculate the WCRC values, the curve is divided into different periods and a straight line is fitted to each segment of the curve. The slope of each straight line represents the WCRC for that period. Fitting a straight line to the curve also implies that WCRC is constant (R) for each segment. This constant R can be used to predict the water cut at any time along that segment with the simple equation of a straight-line.

In order to test its usefulness, the WCRC technique was applied to a project undertaken to conduct detailed pressure transient analysis on 24 Arab-D producers in the Shedgum Leak Area. The aim was to investigate the source of water production in the leaky area.

1. The Shedgum Leak

The Shedgum area of the Ghawar field was first put into production in August 1954. Originally, the Arab-D reservoir pressure was 3200 psig at datum (−6100). However, after the start of production, the reservoir pressure began to decline steadily as a result of continual reservoir depletion without pressure maintenance. By 1968, the Arab-D reservoir pressure dropped to 2250 psig (350 psi above the bubble point pressure). Consequently, peripheral water support was commenced by Gravity Water Injection (GWI) to halt the declining pressure trend. Twenty gravity water injectors were on injection by 1972. However, the reservoir pressure continued to drop even below the bubble point pressure. In 1973, Power Water Injection (PWI) was initiated to effectively overcome and reverse the declining pressure trend and control the water-flood front movement.

The peripheral injectors were situated down-dip of the Arab-D structure. As expected, water breakthrough was reported in the first raw of producers up-dip from injectors. However, a cluster of producers that were located high in the structure away from injectors (in the core dry area of the Shedgum field) started cutting water.

Water production was first noticed in SDGM-47 after one year of production. The surrounding wells SDGM-7, 48, 58, 121 and 171 also started producing wet. This group of wet producers in the interior of the field constituted an area that became later known as the "Shedgum Leak Area."

Nevertheless, other ARMD in-house studies pointed to the possibility of water coming laterally from the north instead. This hypothesis was accepted, since logs taken from new wells drilled north of the leak area supported it. Lateral water encroachment was also supported by the fact that no definite vertical communication channel such as a fault or fracture was confirmed to exist in the leak area.

PTA Results (Study Area)

The results of PTA analysis of wells inside the leaky area indicated the existence of finite conductivity faults. Three wells showed a response similar to that of a conductive fault intersecting the wellbore, and two wells exhibited a response of non-intersecting finite-conductivity fault.

The WCRC test questioned whether these faults are responsible for bringing water into the leaky area through direct communication with the underlying HANIFA reservoir.

Evidence from well logs as to historical water production in the leaky area pointed to lateral water movement from the area north of the leaky area. Therefore, the decision was made to expand the study area to include wells located north, northwest and northeast of the leaky area, with the objective of identifying faults/fractures responsible for the inter-reservoir communication.

However, there were about 60 additional wells in the new study area. To avoid time consuming and cumbersome interpretation, a spatial and temporal analysis of historical water cut behavior was conducted as a guide to anomalous areas of high and hyper water production. The assumption was that wells located closer to a conductive fault/fracture would have a faster rate of WC increase.

Conductive Faults in UTMN

The assumption of the existence of conductive faults in the Shedgum field is supported by many findings and facts. Recent 3-D interpretation has delineated thousands of conductive faults throughout the Ghawar field. Pressure transient analysis of wells in the UTMN field has confirmed the existence of such conductive faults. In the UTMN field, conductive faults poses a challenge to horizontal well drilling. Intersecting conductive faults by horizontal wells will lead to a premature water breakthrough that could start as early as the well is put in production. Conductive faults have been found to act as a communicating channel bringing water from the lower wet zones of Arab-D or even from lower reservoirs.

As an example, a horizontal well was measured that intersected a finite-conductivity fault, where the fault had a high porosity and permeability along the fault plane. A crushed region was created on either side of the fault as a result of the tectonic forces responsible for the faulting process. The region to one side of the fault was of better reservoir quality than the regions on the other side. This was an indication of the fault throw. A production log run on this horizontal well indicated that more than 80% of the total fluid production is coming from the fault plane.

The pressure response of the finite-conductivity fault model on the derivative plot without the effect of skin and wellbore storage effects was then prepared. The flow regimes generated by the model include an early radial around the well. Once the pressure wave reaches the fault plane, it will first encounter the crushed region along the fault. This region acts as a skin on the fault plane causing additional pressure drop responsible for the hump that follow the early radial flow. Next, due to its relatively high conductivity, the fault plane will act as a linear constant pressure support resulting on a negative unit slope on the pressure derivative plot. Finally, when the pressure drop is large enough, fluid from the other region will start moving linearly perpendicular to the fault plane. This will give rise to a bilinear flow regime.

Figure 2:
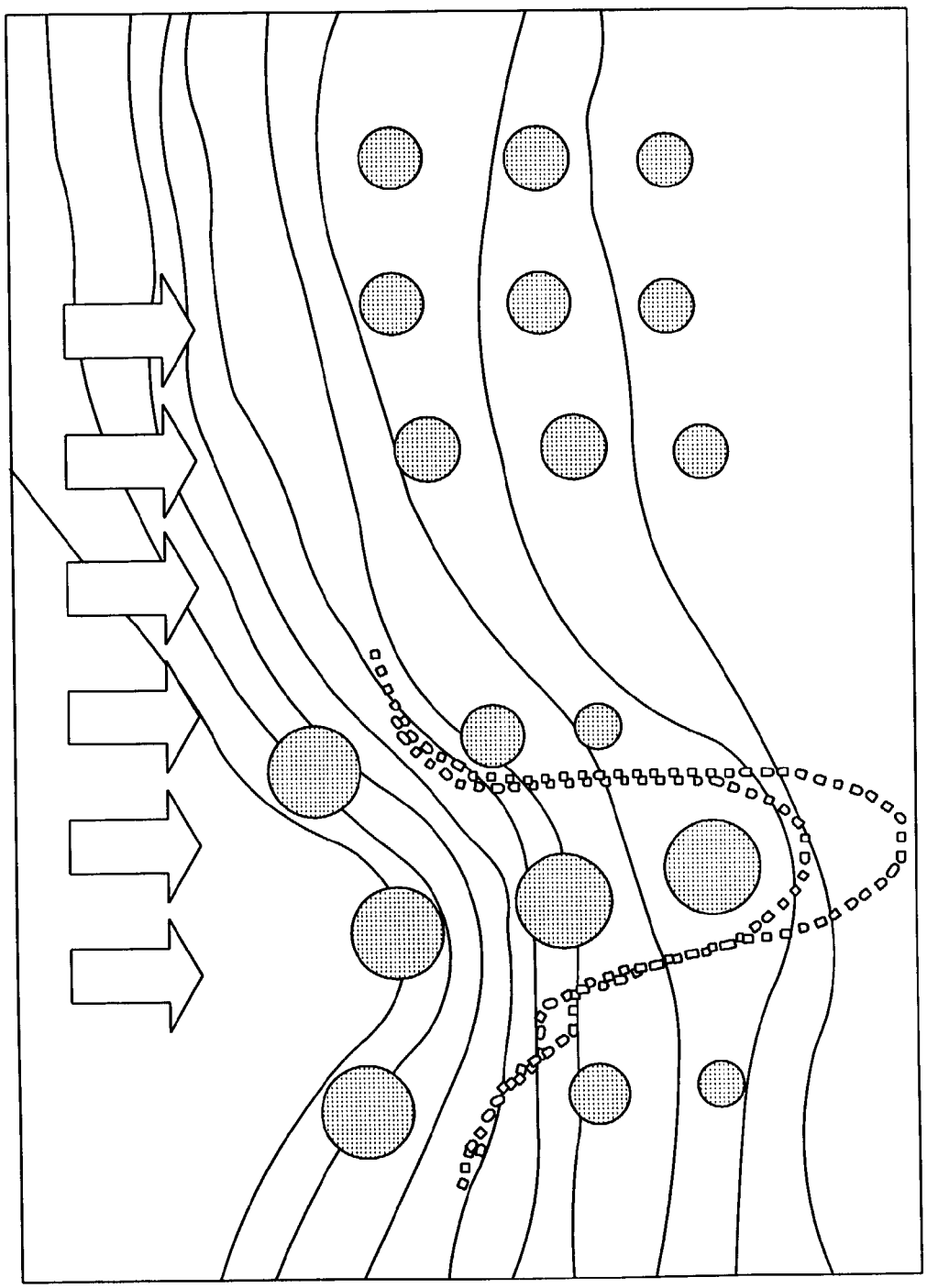
FIG. 2 is an illustration of water flood progress.

FIG. 2 illustrates the effectiveness of the WCRC technique as a qualitative and quantitative analysis tool for the evaluation of water flood progress and the flood front movement.

If there exists an effective water flood with good sweep efficiency, it is expected that a cluster of bubbles will develop on the bubble map such that all the bubbles are of small and comparable sizes. Small sizes will reflect the normal WCRC values due to the effect of water flood advance. The bubbles are also expected to have relatively the same size, which represents an even and effective areal sweep.

On the other hand, if an ineffective water flood with bad sweep efficiency exists, it is expected that a cluster of bubbles will develop such that the bubbles are of different sizes. Small sizes will reflect areas that are ineffectively swept whereas large bubbles indicate areas that are taking most of the injected water and where a water finger is expected to develop.

Looking at the first row of bubbles, which represents the effect of water flood front, it is noted that the center bubble is still larger than the surrounding two. This in turn indicates that water will advance farther in that area, causing the water finger to develop further. Tracking the water flood front with WCRC values can be an early warning that will predict its short term movement (months to few years) before it actually develops. This will yield the opportunity to control either injection or production wells so as to prevent the water finger from developing further and to ultimately improve the areal sweep efficiency.

Figure 3:
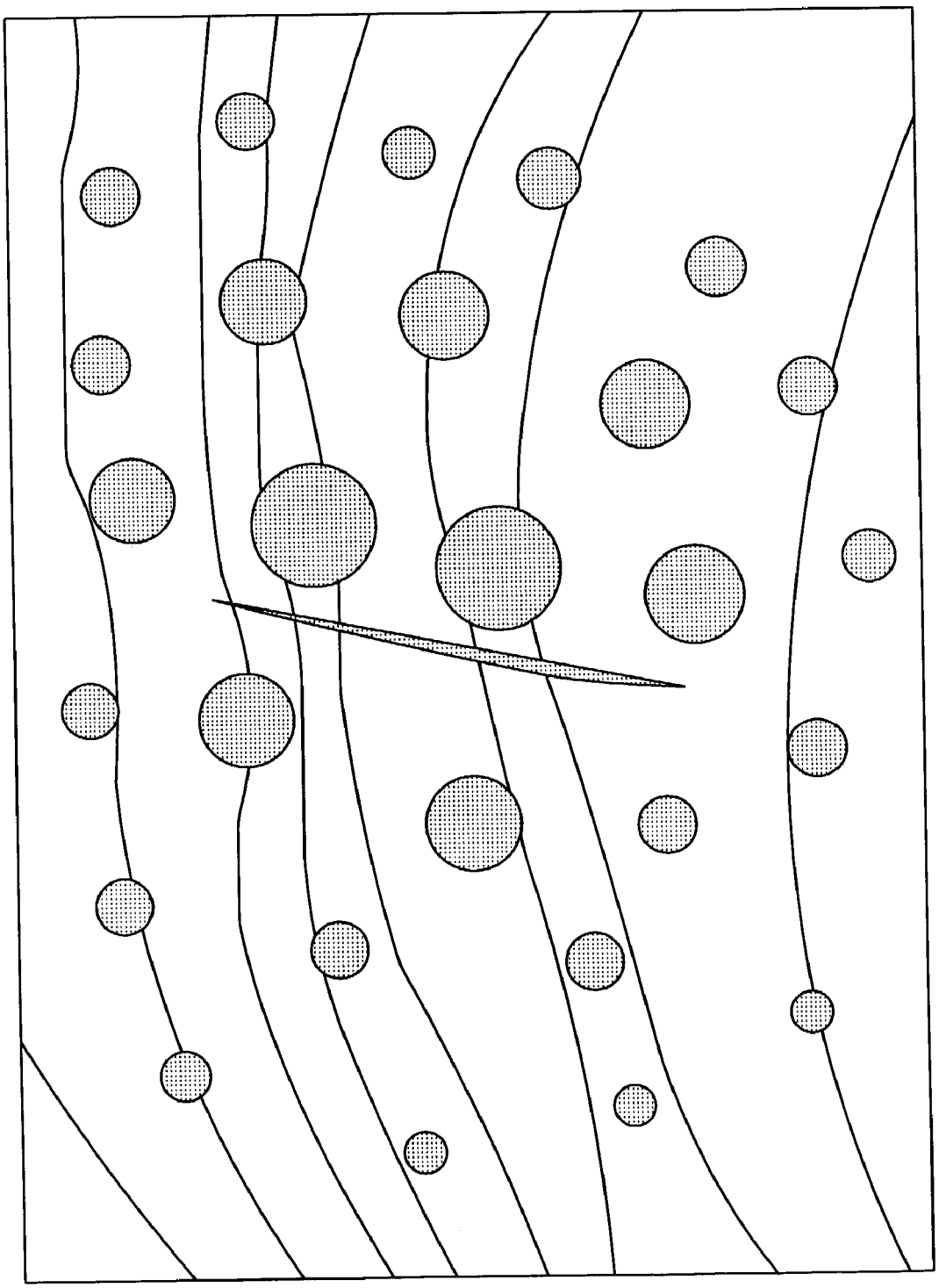
FIG. 3 is an illustration of anomalous area identification.

FIG. 3 illustrates the effectiveness of the WCRC technique as a guide to reservoir flow heterogeneities such as conductive faults and fractures.

If a cluster of bubbles develops such that the largest bubble sizes are located in the center of the cluster, as shown by FIG. 3, and surrounded by concentric rings of smaller and smaller bubble sizes, the following can be concluded, this suggests that water has not migrated laterally from the peripheries. As a matter of fact, the only plausible explanation for such cluster formation is that water is being brought into the area vertically. This in turn could be an indication of the existence of conductive faults or fractures near the center of the cluster and close to wells with the largest WCRC values (bubble sizes). Therefore, identification of areas with hyper WCRC can lead to the delineation of reservoir flow heterogeneities such as faults, fractures and super-k areas. Pressure transient analysis is then utilized to identify these faults/fractures and quantify their flow properties.

WCRC Analysis Limitations

The first limitation is the large scale of the technique. WCRC has the scale of an area/field. Therefore, it has low resolution in the areal perspective. On the other hand, the WCRC technique has no vertical resolution at all. Moreover, the WCRC is not exact, but instead is an averaging process.

The second limitation has to do with WCRC complexity, in that it is a function of many variables. These include injection scheme, production strategies as well as reservoir flow heterogeneities such as conductive faults and fractures and zones with super-permeability.

Case History Application (SDGM-158)

In order to validate the applicability of the new technique, the WCRC method was applied to the offset wells in the area around SDGM-158. Pressure transient analysis of a PI/PBU test conducted on this well pointed to the existence of a nearby finite-conductivity fault as indicated by the response on derivative plot and a good model match. The following question was posed:

If we did not have a prior knowledge about this fault, would the new WCRC technique guide us to it?

PTA (SDGM-158)

Figure 4:
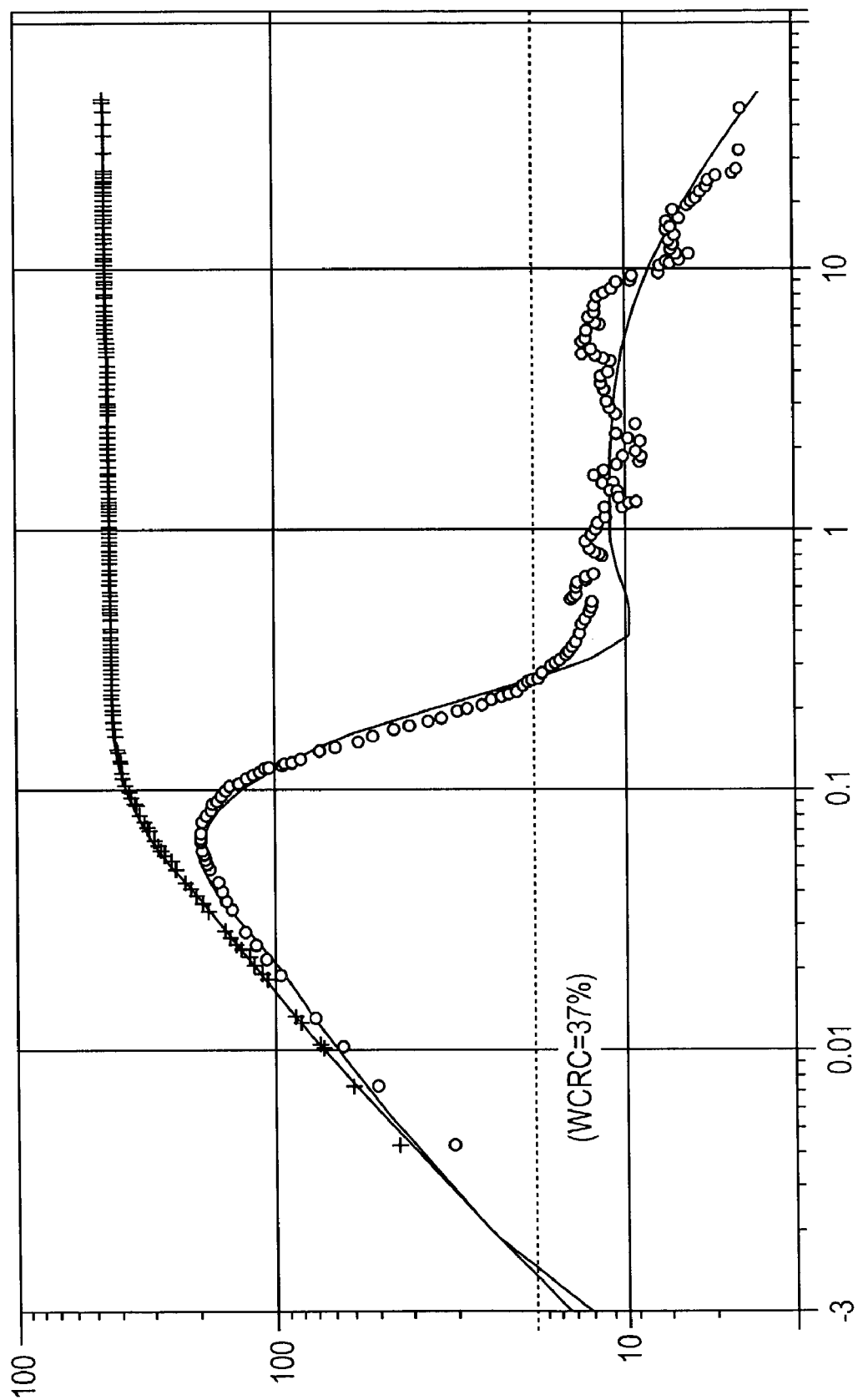
FIG. 4 is a derivative plot for a sample well.

FIG. 4 is a derivative plot from a PI/PBU on SDGM-158. Following the end of the test period, the pressure derivative goes up for a short period creating a hump before it exhibits a downward trend that can be fitted with a straight line of negative unit slope. This response is representative of a non-intersecting finite-conductivity fault or fracture.

Figure 5:
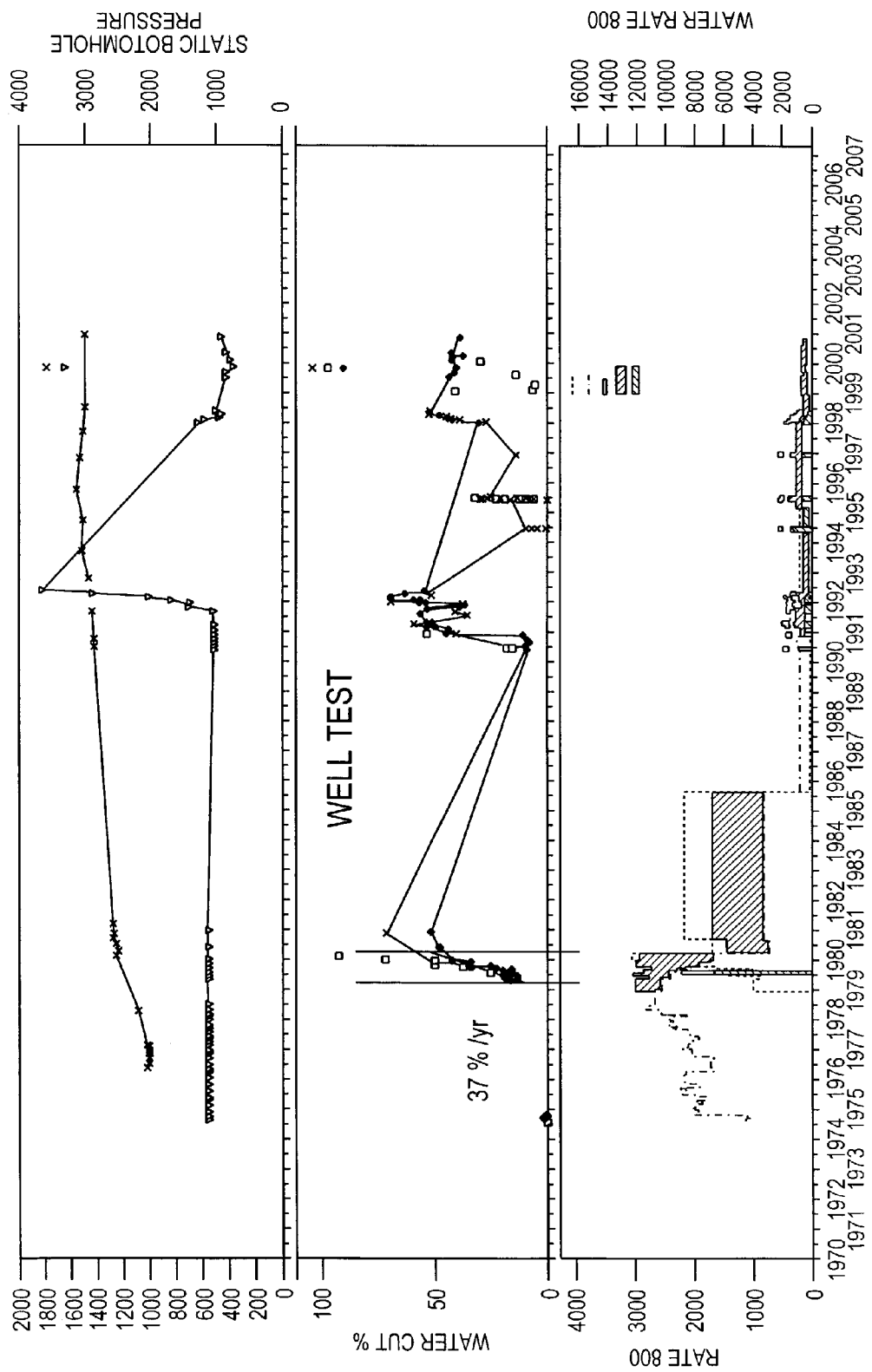
FIG. 5 illustrates anomalous water production for the sample well of FIG. 4.

FIG. 5 shows the anomalous water production at SDGM-158 as indicated by the WCRC of 37%/year.

Identify Anomalies (WCRC>10%)

Applying the new technique to SDGM-158 has resulted in the extremely high WCRC value of 37%. Most offset wells indicated high WCRC values as well. SDGM-1 and 221 had WCRC of 40% per year and SDGM-55 had WCRC of 30% per year.

Figure 6:
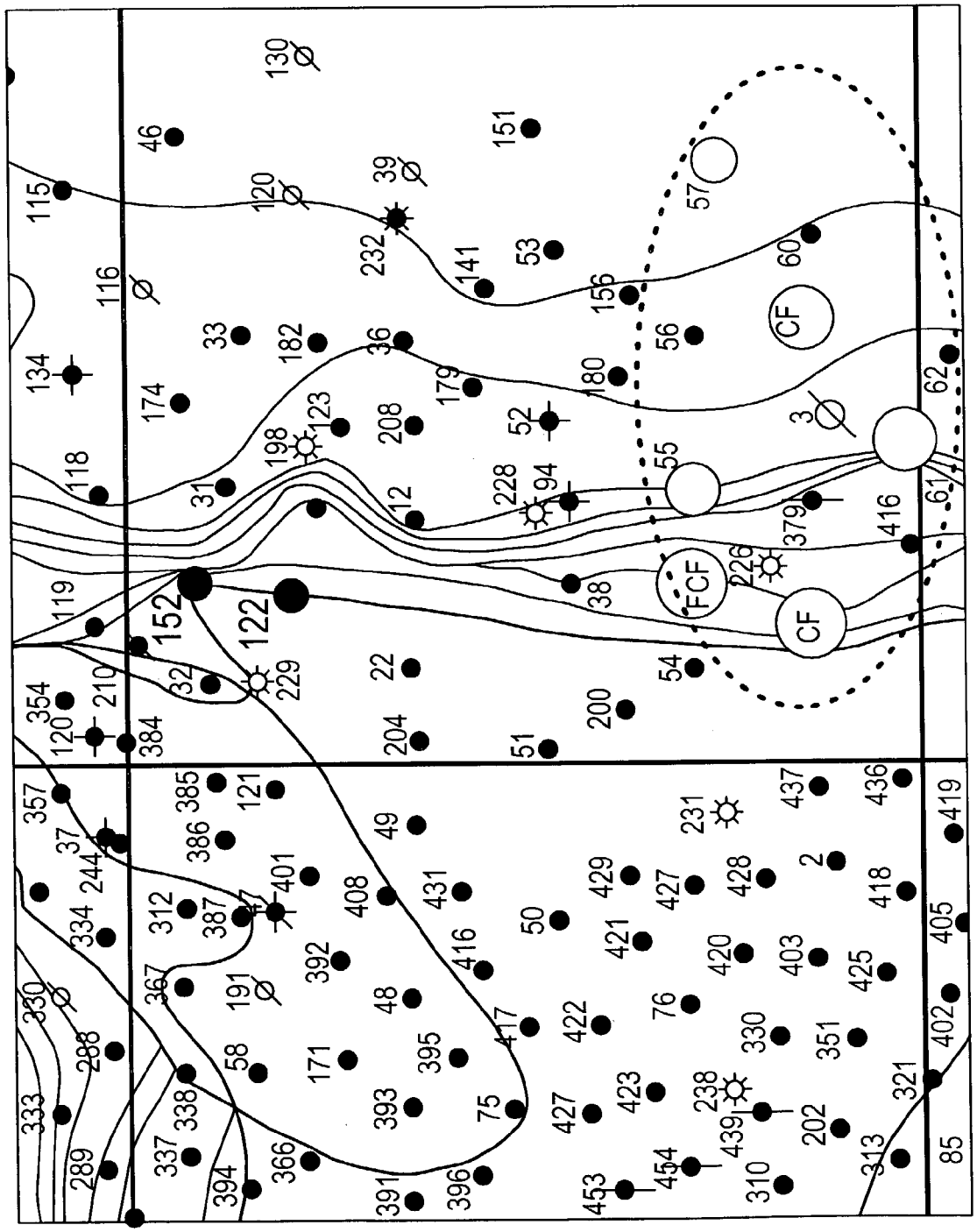
FIG. 6 is a bubble plot for identifying anomalous areas.

The generated bubble map of FIG. 6 clearly confirms the validity of the WCRC technique as a guide to anomalous areas by generating large and concentrated bubble distributions.

These cluster wells are situated at different structural positions with respect to the water-flood front, yet they all exhibit the tendency for hyper water cut increase, as is the case for SDGM-1 and SDGM-221 even though they are located the furthest from the injection line.

Pressure transient analysis of PI/PBU conducted on these anomalous wells in the pilot study area has confirmed this finding and exhibited the signature of both non-intersecting conductive faults at SDGM-1 and one conductive fault/fracture intersecting the wellbore at SDGM-221.

The effectiveness of the WCRC technique is evident from the general agreement of the formed cluster of wells and the location of conductive faults/fractures, as indicated by the pressure transient analysis results.

Once more, while the structural position of the cluster-wells will certainly influence water break-through time, it dos not impact the WCRC values, as was the case earlier for SDGM-1 and SDGM-221. This fact is best illustrated by the historical water cut trend of these cluster-wells, as shown by FIG. 7.

Figure 7:
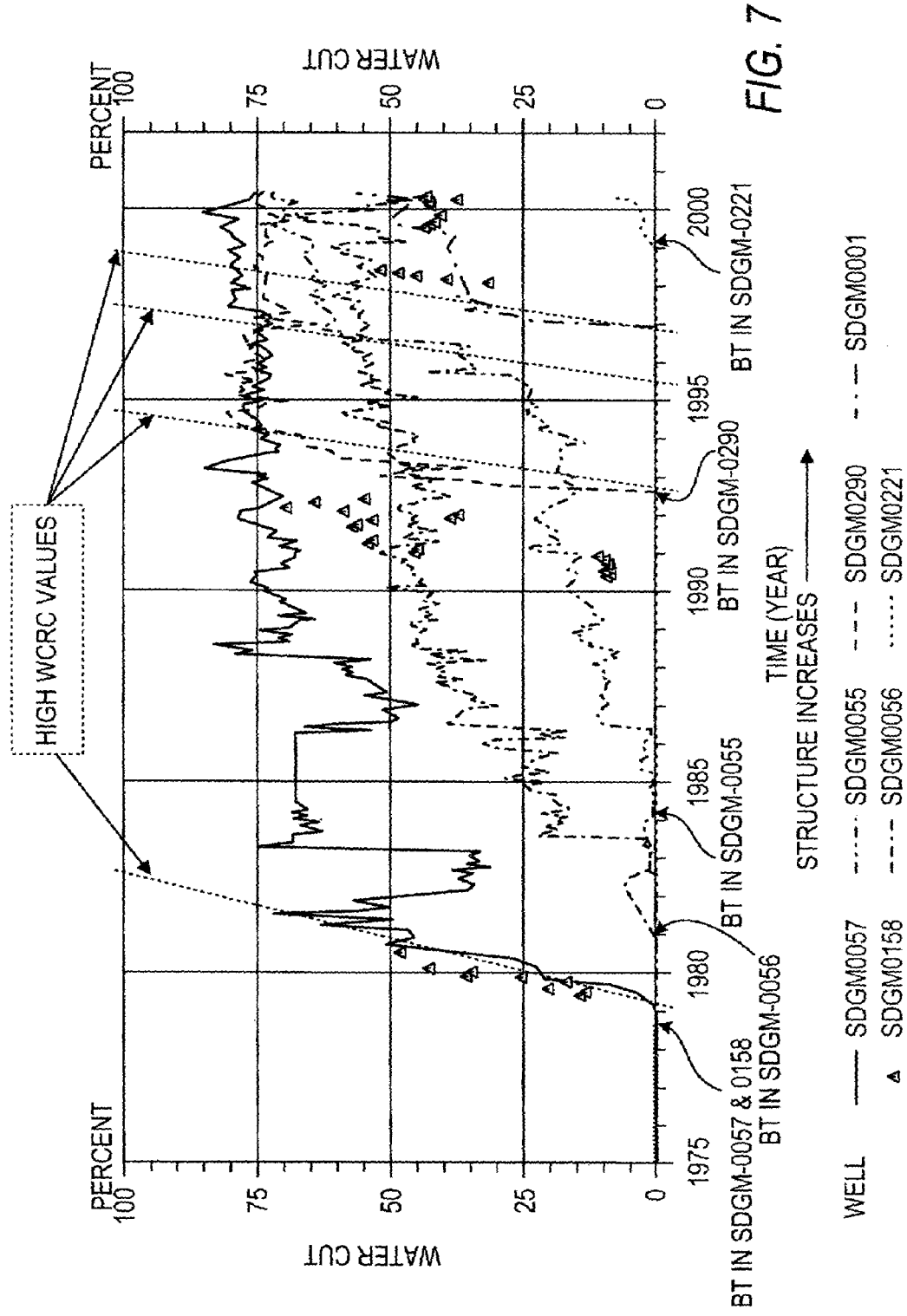
FIG. 7 is a plot relating water cut to increasing structure.

It is clear from FIG. 7 that while water breakthrough is a function of structural position, the calculated high WCRC values at SDGM-55, 57, 158, 290 and 1 and 221, as defined by the orange dotted lines, are not. Instead, fracture/fault signatures were confirmed through pressure transient analysis in three of these six wells or 50% of the total (SDGM-158, 1 and 221). Furthermore, the remaining three wells (SDGM-55, 57 and 290) had no or bad test data (dynamic wellbore phenomena) that prevented model identification, which obscured meaningful pressure transient interpretation.

WCRC Performance (Study Area)

After the new WCRC technique was validated, it was applied in the areas of interest north, northeast and northwest of the Shedgum Leak Area.

WC Performance (WCRC>10%)

WCRC was calculated for all wells in the expanded study area. The results are represented by the dark blue bubbles, as shown on FIG. 8, where the relative size of the bubbles corresponds to their calculated WCRC. A WCRC cutoff value of 10%/year was used (only wells with WCRC>10%/year are plotted).

Figure 8:
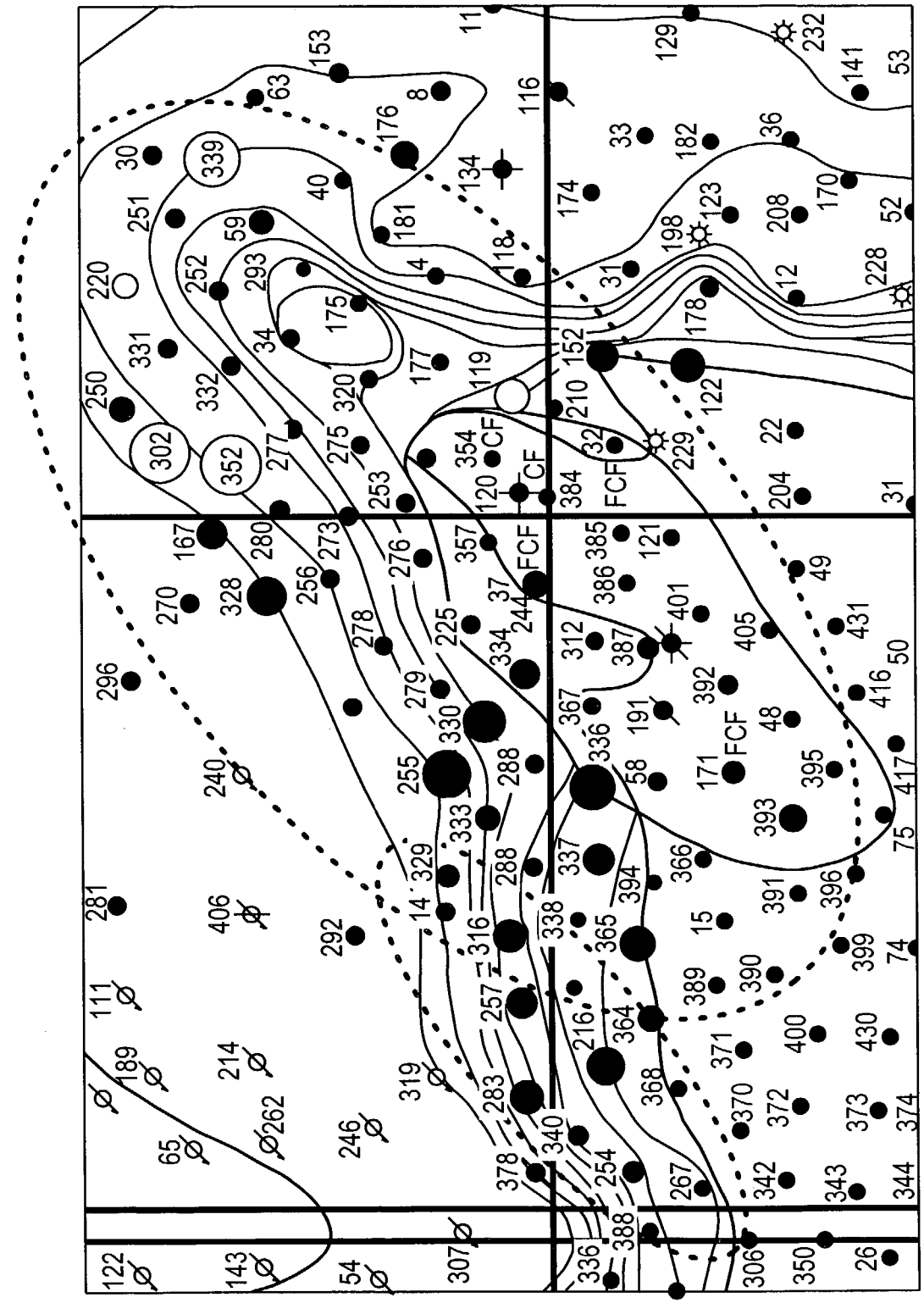
FIG. 8 is a bubble plot of the water cut rates of change for the Shedgum Leak Area.

FIG. 8 illustrates the formation of two clusters of wells concentrated northeast and northwest of the Shedgum Leak area. These clusters of wells represent the most anomalous regions of hyper water production.

Therefore, attention was focused on these anomalous wells and pressure build up data was retrieved for those wells within the clusters only. Twenty-one new wells in total were added to the previous 23 leak area wells. Detailed pressure transient analysis of these new wells was performed.

When the WCRC cutoff value to was raised to 15%/year, the same clusters as for the 10% case were obtained.

Figure 9:
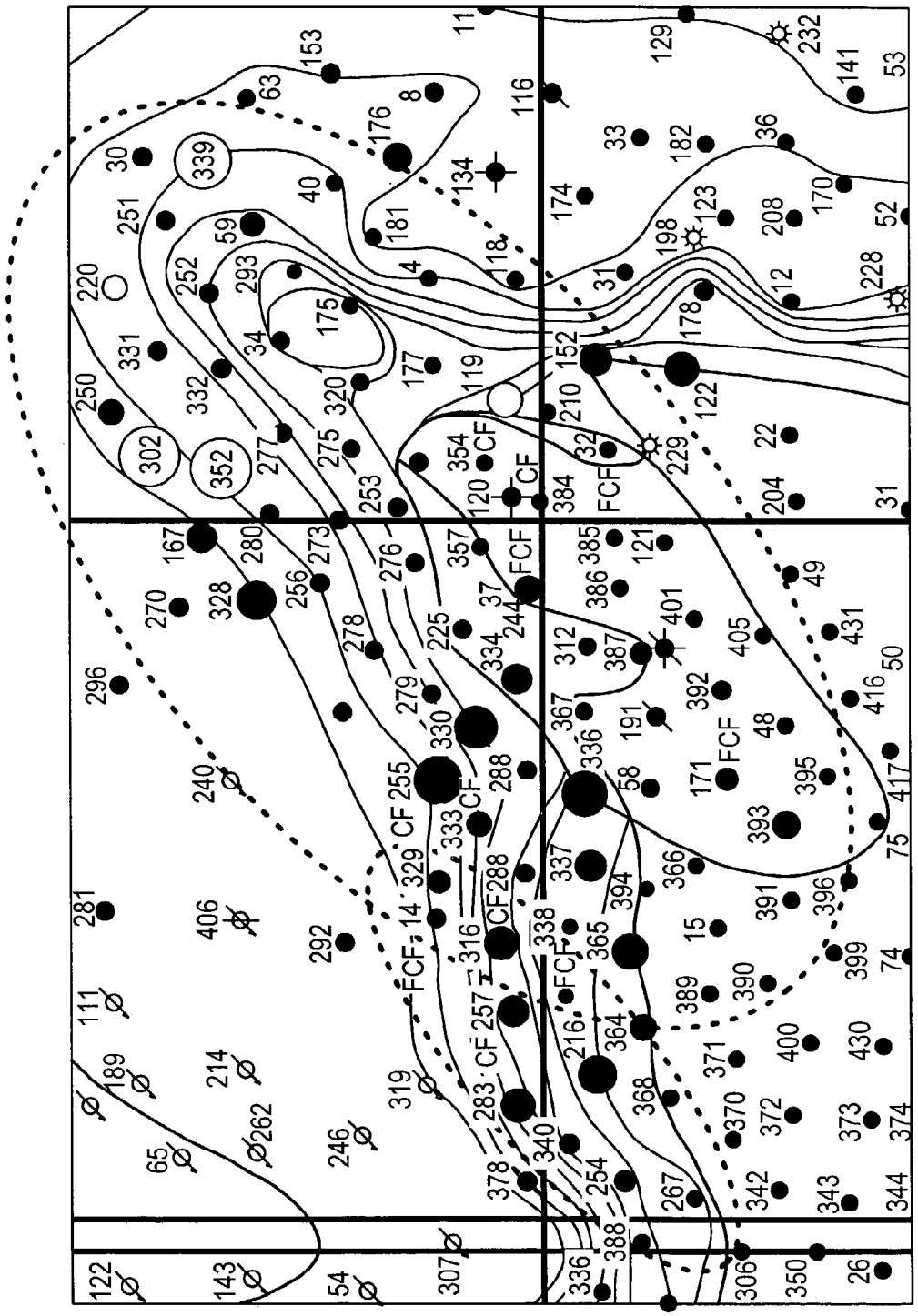
FIG. 9 is a bubble plot showing the results of pressure transient analysis for the Shedgum Leak Area.

FIG. 9 shows the results of pressure transient analysis on the anomalous wells.

It is possible to unambiguously identify several conductive faults and fractures intersecting and non-intersecting six wells (29% of the total 21 wells). SDGM-14 and SDGM-269 exhibited a response of intersecting finite conductivity fault/fracture (ICF). In the mean time, four other wells (SDGM-239, 255, 257 & 316), located in the same cluster to the northwest of the leak area, exhibited a response of non-intersecting finite conductivity fault/fracture (NICF).

3-D Seismic Interpretation

Once the pressure transient analysis confirmed the existence of conductive faults and fractures in that area, as the WCRC technique was suggesting, a recent 3-D seismic reinterpretation was reviewed, which delineated two sets of non-connecting conjugate faults of orthogonal trends to the NW.-SE. and NE.-SW. Seismic re-processing has also shown that some of these faults are traced down all the way to Hanifa or even deeper reservoirs.

Faults inside the leak area may have been responsible for early water production inside the leak area. Faults located northwest have come into the picture at a later stage and are suspected to have played an even more important role as conduits to inter-reservoir communication.

Figure 10:
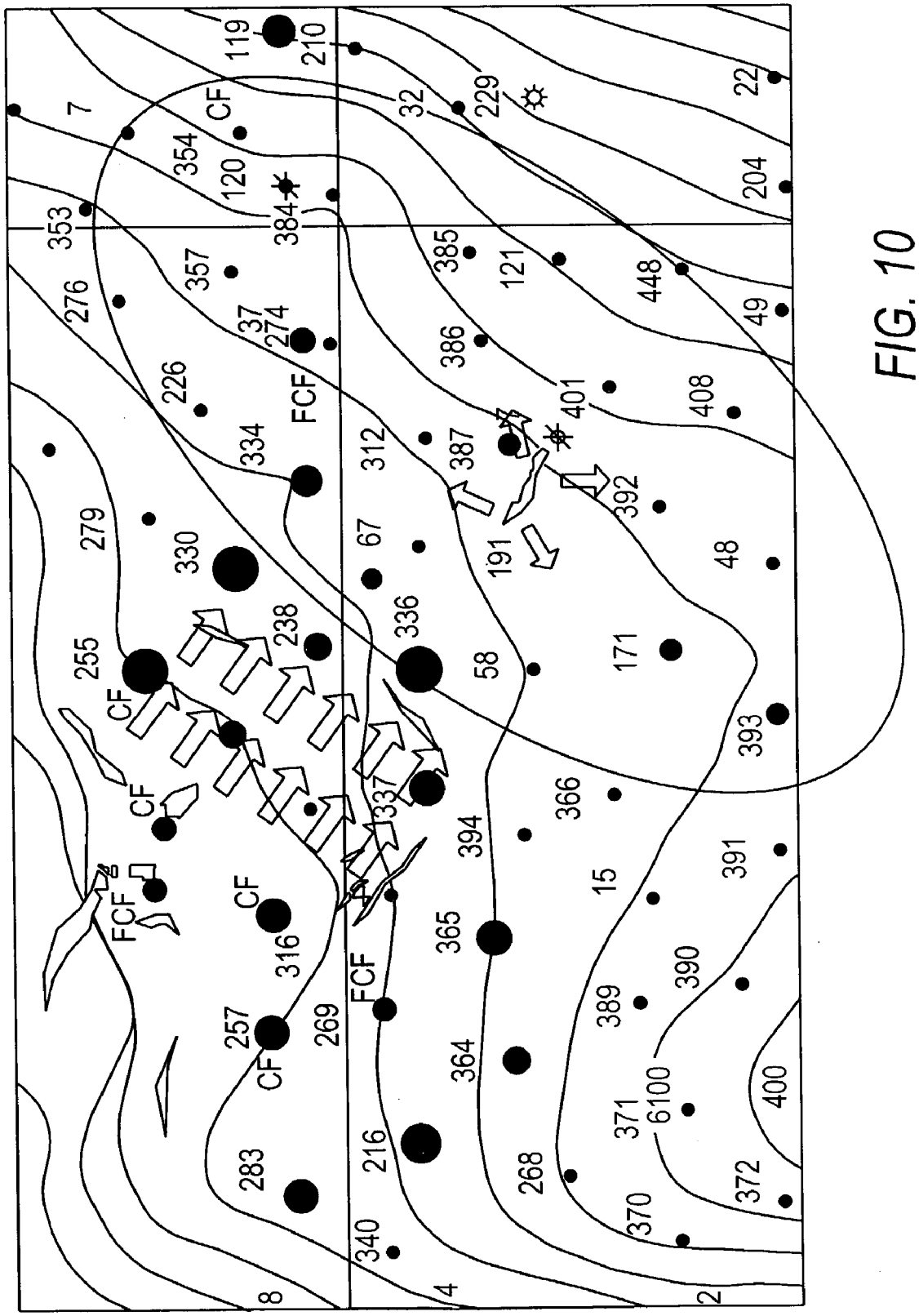
FIG. 10 is a 3-D seismic interpretation based on the water cut rates of change for the Shedgum Leak Area.

Therefore, seismic interpretation has yielded the same findings and conclusions resulting from both WCRC and pressure transient analysis, confirming the existence of conductive faults/fractures in this heavily faulted and fractured region located to the northwest in addition to these already delineated within the leak area. These new findings resulting from the WCRC, well testing and 3-D seismic measurements are plotted on the same map as shown in FIG. 10, where the location of the leak area is shown by the red oval.

Based on the results of this study, it is believed that water was migrating vertically from lower reservoirs (Hanifa) into Arab-D reservoir through the conductive faults delineated inside the leak area first, then from the region located to the NW. Once in Arab-D, water then moved laterally within the area and southeast into the leak area as a result of continuous and considerable pressure depletion of areas to the south. The arrows within the leak area represent the proposed water migration path during early years of production. On the other hand, arrows northwest of the leak area point to the source and path of yet more water encroachment into the leak area at a later stage.

CONCLUSIONS

The water cut rate of change (WCRC) analysis technique is a new and powerful tool that will enhance the overall exploitation of hydrocarbons reserves.

The WCRC method provides insightful and valuable information that can be utilized to improve reservoir management, reservoir characterization, reservoir simulation and production strategies.

The WCRC can aid and facilitate well testing and seismic interpretation.

The WCRC technique is quick, easy to use and flexible diagnostic method that can be improved or modified to suit particular applications or different locations.

The WCRC technique has several applications such as identification of reservoir flow heterogeneities and evaluation and short-term prediction of water flood progress and areal sweep efficiencies.

In the above embodiments, WCRC was graphically calculated as a constant in a segmented approach and was plotted manually as a bubble map. The same WCRC technique can be automated and more accurately calculated using a computer program that will calculate the continuous derivative by one or the well known and available mathematical algorithms. The next stage would be to have the program plot of the resulting WCRC values on the same map. Automation of WCRC calculation and plotting will dramatically improve the speed and accuracy of the technique.

The continuous derivative (WCRC) of historical trend will yield values that are not constant, but changing with time instead. The continuous derivative method can still be utilized in the same manner highlighted by the segmented approach. In both methods, a minimum of one-year historical trend should be utilized to calculate representative WCRC values. Therefore, calculated WCRC values represent a minimum of one-year period, but the same trend can actually be observed over several years. This fact points to another area of improvement where the WCRC values can be further classified on the basis of their duration. Hence, wells with a WCRC value of 20% over a three-year period should be considered more anomalous than wells having a WCRC value of 20% over one or two years. For that reason, while the WCRC principle is the same, different applications will require certain modifications in order to make the technique more accurate and robust.

The WCRC technique has the following applications:
  a. Evaluate past and present water flood progress and areal sweep efficiency performance using the WCRC analysis technique.
  b. Identify reservoir flow heterogeneities such as faults, fractures and high permeability layers (super-k) using the WCRC analysis technique by identifying anomalous areas of hyper water production.
  c. Make short term prediction (months to few years) of future water cut behavior from past and current WCRC values.
  d. Make short term projection (months to few years) of future flood front advancement and expected areal sweep from past and current WCRC values.

While the disclosed method has been particularly shown and described with respect to the preferred embodiments, it is understood by those skilled in the art that various modifications in form and detail may be made therein without departing from the scope and spirit of the invention. Accordingly, modifications such as those suggested above, but not limited thereto are to be considered within the scope of the invention, which is to be determined by reference to the appended claims.

I claim:

1. A method of identifying the existence of a water effect anomaly of an underground non-water well comprising the steps of:
  assembling a history of water cut (WC) measurements for the well over an extended period of time (t);
  determining a water cut rate of change (R) for the well based upon the history of water cut measurements, wherein the water cut rate of change (R) is determined as follows:

$$\frac{d(WC)}{d(t)} = R;$$

identifying that a water effect anomaly exists when the determined R exceeds a predetermined water cutoff rate of change (WCRC) cutoff value.

2. The method of claim 1, wherein R is determined as a constant.

3. The method of claim 2, wherein R is determined as a constant.

4. The method of claim 1, wherein an updated water cut $WC_{new}$ is determined from a prior water cut $WC_1$ as follows:

$$WC_{new} = WC_1 + Rt,$$

where t is an elapsed time between $WC_{new}$ and $WC_1$.

5. The method of claim 1, wherein said identifying step includes the step of visually presenting the determined water cut rate of change on a bubble map.

6. The method of claim 1, wherein the well is an oil well.

7. The method of claim 1, wherein the anomaly is an anomalous area.

8. The method of claim 1, wherein the predetermined WCRC cutoff value is 10%.

9. A method of identifying the existence of a water effect anomaly in a geographical area containing a plurality of underground non-water volumes comprising the steps of:
   for each volume, assembling a history of water cut (WC) measurements for the volume over an extended period of time (t);
   determining a water cut rate of change (R) for each volume based upon the respective history of water cut measurements, wherein the water cut rate of change (R) is determined as follows:

$$\frac{d(WC)}{d(t)} = R;$$

and
   for each volume identifying that a water effect anomaly exists when the volume's determined R exceeds a predetermined water cut rate of change (WCRC) cutoff value.

10. The method of claim 9, wherein each R is determined as a constant.

11. The method of claim 9, wherein said identifying step includes the step of visually presenting the determined water cut rates of change on a bubble map.

12. The method of claim 9, wherein an updated water cut $WC_{new}$ is determined from a prior water cut $WC_1$ as follows:

$$WC_{new} = WC_1 + Rt,$$

where t is an elapsed time between $WC_{new}$ and $WC_1$.

13. The method of claim 12, wherein each R is determined as a constant.

14. The method of claim 13, wherein each well is an oil well.

15. The method of claim 9, wherein each of the volumes is a well.

16. The method of claim 9, wherein each anomaly is an anomalous area.

17. The method of claim 9, wherein the predetermined WCRC cutoff value is 10%.

* * * * *